United States Patent [19]

Suzuki et al.

[11] Patent Number: 4,465,872

[45] Date of Patent: Aug. 14, 1984

[54] PROCESS FOR PRODUCING P-CRESOL

[75] Inventors: Takashi Suzuki; Shoichiro Hashimoto; Masami Orisaku; Rieko Nakano, all of Niigata, Japan

[73] Assignee: Mitsubishi Gas Chemical Company, Inc., Tokyo, Japan

[21] Appl. No.: 391,445

[22] Filed: Jun. 23, 1982

[30] Foreign Application Priority Data

Sep. 8, 1981 [JP] Japan .................................. 56-141378

[51] Int. Cl.³ ............................................... C07C 37/56
[52] U.S. Cl. .................................... 568/803; 568/741; 568/771
[58] Field of Search ........................ 568/803, 741, 771

[56] References Cited

U.S. PATENT DOCUMENTS

| | | | |
|---|---|---|---|
| 3,872,156 | 3/1975 | Bourdin et al. | 568/803 |
| 3,875,247 | 4/1975 | Bourdin et al. | 568/803 |
| 3,927,122 | 12/1975 | Bourdin | 568/803 |
| 3,927,123 | 12/1975 | Bourdin et al. | 568/803 |

*Primary Examiner*—Werren B. Lone
*Attorney, Agent, or Firm*—Armstrong, Nikaido, Marmelstein & Kubovcik

[57] ABSTRACT p-Cresol is produced in one step by direct oxidation of p-tolualdehyde with a peroxide in formic acid as a solvent while keeping 3 to 15% by weight of water in formic acid on the basis of formic acid and a reaction temperature in a range of 50° to 150° C.

11 Claims, No Drawings

PROCESS FOR PRODUCING P-CRESOL

BACKGROUND OF THE INVENTION

This invention relates to a process for producing p-cresol by direct oxidation of p-tolualdehyde with a peroxide such as hydrogen peroxide or performic acid.

p-Cresol is an important raw material for plastic and also important intermediate for industrial chemicals, medicines, agricultural chemicals, etc.

p-Cresol can be produced according to a separation process from tar acids, or various synthesis processes including the cymene process.

Generally, alkylphenols are not so different from one another in physical properties, for example, between their isomers, or even between their homologs. p-Cresol of high purity is thus hard to obtain according to the separation process.

On the other hand, the synthetic processes also have disadvantages. For example, isomers are formed as by-products or the wastes must be disposed in the sulfonation-alkali fusion process or complicated apparatuses are required in the cymene process.

Apart from the processes described above, a process based on the Baeyer-Villiger reaction is well known for synthesizing cresyl formate by oxidizing p-tolualdehyde with a peracid such as hydrogen peroxide. The said process is suitable for synthesizing p-cresol of high purity, and is regarded as an attractive process for preparing p-cresol in view of the recent success in commercial production of p-tolualdehyde by carbonylation of toluene. In this connection, a process for oxidizing p-tolualdehyde with a carboxylic peracid having a pKa below 4 in water has been proposed (see U.S. Pat. No. 3,927,123), wherein, when performic acid derived from hydrogen peroxide is used, the reaction proceeds as follows:

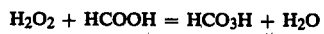

$$H_2O_2 + HCOOH = HCO_3H + H_2O \quad (1)$$

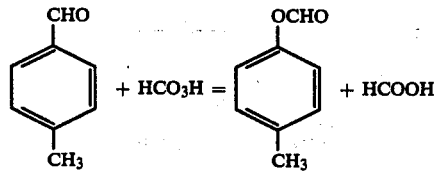

Overall reaction equation can be expressed as follows:

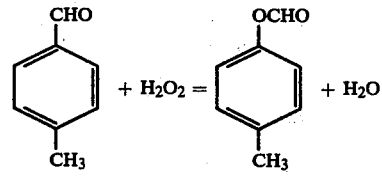

In the process, cresyl ester and water are formed by oxidizing p-tolualdehyde, and a step for hydrolyzing the ester is indispensable for the preparation of p-cresol. Furthermore, the water content of the medium increases as the reaction proceeds, resulting in lowering in the reaction rate. Due to these disadvantages the process is still unsatisfactory as a commercial process in spite of its distinguished selectivity.

As a result of extensive studies made of a commercial process for preparing p-cresol from p-tolualdehyde, the present inventors have found that p-tolualdehyde can be directly converted to p-cresol by oxidizing p-tolualdehyde in formic acid solvent under specific conditions, and have established the present invention.

SUMMARY OF THE INVENTION

The present invention is to provide a process for preparing p-cresol by oxidizing p-tolualdehyde with a peroxide in formic acid solvent, which comprises conducting the oxidation while keeping (i) a water content of the formic acid solvent at 3 to 15% by weight (based on formic acid) and (ii) a reaction temperature in a range of 50° to 150° C.

The present process can be expressed by the following reaction equations:

When hydrogen peroxide is used as a peroxide:

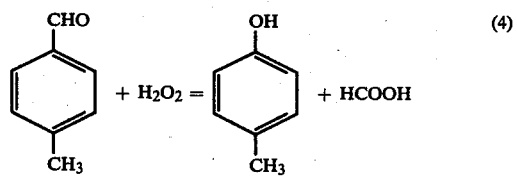

When performic acid is used as a peroxide:

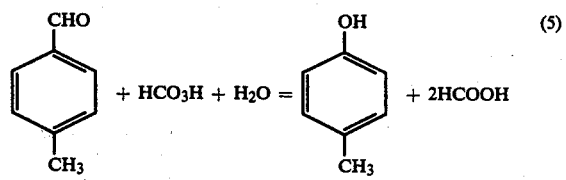

p-Cresol can be directly obtained from p-tolualdehyde.

The peroxide for use in the present invention may be performic acid or hydrogen peroxide. Performic acid, so long as it is synthesized by any of the well-known processes, can be used. Particularly, a performic acid solution in formic acid prepared by contacting a hydrogen peroxide solution in formic acid with an acid catalyst is preferable, because it contains equimolar amounts of water and performic acid, and the reaction expressed by the foregoing equation (5) can be carried out directly with the performic acid solution.

The present invention is characterized in that hydrogen peroxide can be used as a peroxide. Hydrogen peroxide as such or as a solution in formic acid is fed to the reaction system. Performic acid, though partly formed in a hydrogen peroxide solution in formic acid, is not substantially formed in the absence of an acid catalyst and in a short residence time.

The water content of the formic acid solvent is important to the present process. In order to obtain p-cresol directly from p-tolualdehyde, the water content of the formic acid must be 3 to 15% by weight (based on formic acid), and the reaction temperature must be 50° to 150° C.

If the water content is below 3% by weight, p-cresol cannot be obtained directly, and most of the tolualdehyde is converted into cresyl ester. If the water content is above 15% by weight, selective conversion of p-tolualdehyde to p-cresol is inhibited, increasing the yield of p-toluic acid.

In the present invention, the reaction temperature is in a range of 50° to 150° C. If the reaction temperature is below 50° C., the rate of formation of p-cresol from p-tolualdehyde is low and is not practical. If, on the other hand, the reaction temperature exceeds 150° C., the selectivity is reduced in the reaction.

The raw material for use in the present invention is p-tolualdehyde, which may contain o- or m-isomer thereof. Preferable p-tolualdehyde is the one synthesized by oxidizing p-xylene or carbonylating toluene. In the present invention, p-cresol with the same isomer content as that of raw material can be obtained.

In the present invention, the reaction can be carried out in a homogeneous liquid phase. Since the reaction is exothermic, the heat corresponding to the released heat must be removed to maintain the reaction temperature. Usually, the heat is removed preferably through a heat transfer surface of an internal or external heat exchanger.

However, it is most preferable to remove the heat through the latent heat of evaporation of the solvent by carrying out the oxidation under a reduced or increased pressure corresponding to the vapor pressure of the solvent (formic acid and water) at a given reaction temperature of 50° to 150° C., and by refluxing the condensed solvent vapor to the reaction system.

The amount of hydrogen peroxide or performic acid for use in the present invention is not fixed, but when preference is made to the conversion of p-tolualdehyde, a molar ratio of hydrogen peroxide or performic acid to p-tolualdehyde should be in a range of 1.00 to 2.00, preferably 1.01 to 1.30.

The amount of formic acid solvent for use in the present invention must be set to give a water content of 3 to 15% by weight of the formic acid solvent (based on the formic acid), and usually formic acid is used in an amount of 3 to 10 times the weight of p-tolualdehyde.

It is not always necessary to use a catalyst in the present invention, but use of an acid catalyst may have some effects, and particularly use of a solid acid catalyst, such as zeolite or an ion exchange resin, is preferable.

The reaction mixture obtained according to the present process contains p-cresol, formic acid and water, and further contains small amounts of other high-boiling by-products. The formic acid and water are removed from the reaction mixture first, and then the desired product p-cresol is separated from the high-boiling residues. On the other hand, formic acid and water are distilled in a distillation column to adjust the water content in the formic acid to be recycled to the reaction system and to discharge the formic acid formed by the reaction and the water brought in the reaction system by the hydrogen peroxide. The recovered formic acid can be reused.

According to the present invention, p-cresol can be obtained from p-tolualdehyde in one step, and less change in the water content of the formic acid solvent permits the reaction to proceed at a stable reaction rate.

PREFERRED EMBODIMENTS OF THE INVENTION

EXAMPLE 1

Charged into a three-necked flask provided with a stirrer, a reflux condenser and a dropping funnel are 216.8 g of formic acid with a moisture content of 1% by weight or less, 25.6 g of water and 40.0 g of p-tolualdehyde. The resulting mixture is heated on a water bath while keeping an inside pressure of the flask under 200 mmHg by an evacuation apparatus connected to the reflux condenser. After an inside temperature of the flask becomes constant at 60° C. and refluxing and vaporization become stable, 15.1 g of 90% hydrogen peroxide is added to the flask from the dropping funnel for about 5 minutes. Heat is released through the reaction initiated by addition of hydrogen peroxide, but the inside temperature of the flask is kept constant by refluxing. After the addition is finished, the reaction mixture is kept as it is for 60 minutes. A sample is then taken out of the flask for analysis by gas chromatography. Results are shown in Table 1.

EXAMPLE 2

Reaction is carried out in the same manner as in Example 1, except that a performic acid solution in formic acid is used in place of the 90% hydrogen peroxide in Example 1. Molar ratio of the reactants and results are shown also in Table 1.

EXAMPLE 3

Reaction is carried out in the same manner as in Example 1 except that 40 g of zeolite is added to the flask. Results are shown also in Table 1.

COMPARATIVE EXAMPLES 1-3

Reaction is carried out in the same manner as in Example 1 except that reaction temperature and the water content in the formic acid solvent are changed. Reaction conditions and results are shown in Table 2.

EXAMPLES 4-5

Reaction is carried out in the same manner as in Example 1 except that the reaction temperature and the water content in the formic acid solvent are changed. Reaction conditions and results are shown also in Table 1.

TABLE 1

| Example No. | 1 | 2 | 3 | 4 | 5 |
|---|---|---|---|---|---|
| Reactants | | | | | |
| Formic acid g (mol) | 216.8 (4.710) | 216.8 (4.710) | 216.8 (4.710) | 216.8 (4.710) | 216.8 (4.710) |
| $H_2O$ g (mol) | 27.1 (1.506) | 27.1 (1.506) | 27.1 (1.506) | 13.5 (0.750) | 27.1 (1.506) |
| $H_2O_2$ g (mol) | 13.6 (0.400) | 1.4 (0.040) | 13.6 (0.400) | 13.6 (0.400) | 13.6 (0.400) |
| Performic acid (mol) | — | 22.3 (0.360) | — | — | — |
| p-Tolualdehyde (mol) | 40.0 (0.333) | 40.0 (0.333) | 40.0 (0.333) | 40.0 (0.333) | 40.0 (0.333) |
| Catalyst | | | | | |
| | — | — | Zeolite 40 g | — | — |
| Reaction conditions | | | | | |
| Temperature (°C.) | 60 | 60 | 60 | 60 | 90 |
| Pressure (mmHg) | 200 | 200 | 200 | 200 | 550 |
| Time (min) | 65 | 65 | 65 | 65 | 30 |
| Results | | | | | |
| Water content after the completion of reaction (based on formic acid) % by weight | 12 | 12 | 12 | 6 | 12 |
| Conversion of p-tolualdehyde % | 100 | 100 | 100 | 100 | 100 |
| Selectivity to p-cresol (based on p-tolualdehyde) % | 85.5 | 92.3 | 91.5 | 84.5 | 85.0 |

TABLE 2

| | Comparative example | 1 | 2 | 3 |
|---|---|---|---|---|
| Reactants | Formic acid g (mol) | 216.8 (4.710) | 216.8 (4.710) | 240.9 (5.234) |
| | H₂O g (mol) | 27.1 (1.506) | 27.1 (1.506) | 1.5 (0.093) |
| | H₂O₂ g (mol) | 13.6 (0.400) | 13.6 (0.400) | 13.7 (0.403) |
| | Performic acid g (mol) | — | — | — |
| | p-Tolualdehyde g (mol) | 40.0 (0.333) | 40.0 (0.333) | 40.0 (0.333) |
| Catalyst | | — | Zeolite 40 g | — |
| Reaction conditions | Temperature (°C.) | 20 | 20 | 50 |
| | Pressure (mmHg) | 760 | 760 | 200 |
| | Time (min) | 120 | 120 | 120 |
| Results | Water content after the completion of reaction (based on formic acid) % by weight | 12 | 12 | 1 |
| | Conversion of p-tolualdehyde % | 100 | 100 | 100 |
| | Selectivity to p-cresol (based on p-tolualdehyde) % | 45.1 | 60.0 | 73.2 |

What is claimed is:

1. A process for producing p-cresol, which comprises oxidizing p-tolualdehyde in a formic acid solvent with hydrogen peroxide or performic acid, while maintaining a water content in the formic acid solvent of 3 to 15% by weight on the basis of formic acid, and at a reaction temperature at 50° to 150° C.

2. The process according to claim 1, wherein the performic acid is a performic acid solution in formic acid obtained by contacting a hydrogen peroxide solution in formic acid with an acid catalyst.

3. The process according to claim 1, wherein the p-tolualdehyde contains o-isomer or m-isomer.

4. The process according to claim 1, wherein the oxidation is carried out while removing the released heat of reaction.

5. The process according to claim 4, wherein the released heat is removed through surface heat transfer of an internal or external heat exchanger.

6. The process according to claim 4, wherein the released heat is removed through the latent heat of evaporation of the solvent by conducting the oxidation under a reduced or increased pressure corresponding to the vapor pressure of the solvent at a given reaction temperature of 50° to 150° C., and by refluxing the condensed solvent vapor.

7. The process according to claim 1, wherein a molar ratio of the peroxide to p-tolualdehyde is 1.00 to 2.00.

8. The process according to claim 1, wherein the formic acid solvent is used in an amount of 3-10 times the weight of the p-tolualdehyde.

9. The process according to claim 1, wherein the oxidation is carried out in the presence of an acid catalyst.

10. The process according to claim 9, wherein the acid catalyst is a solid acid catalyst.

11. The process according to claim 10, wherein the solid acid catalyst is zeolite or ion exchange resin.

* * * * *